United States Patent [19]
Kawakami et al.

[11] 3,955,929
[45] May 11, 1976

[54] GAS DETECTING SENSOR

[75] Inventors: Takaya Kawakami; Toshinori Kitamura, both of Kyoto; Nobuyuki Yamaji, Takatsuki, all of Japan

[73] Assignee: Nichicon Capacitor Limited, Kyoto, Japan

[22] Filed: Oct. 18, 1974

[21] Appl. No.: 515,887

[30] Foreign Application Priority Data
Oct. 19, 1973 Japan............................. 48-117444

[52] U.S. Cl............................. 23/254 E; 23/255 E; 73/27 R; 252/408
[51] Int. Cl.² ................... G01N 27/04; G01N 27/14
[58] Field of Search .......... 23/232 R, 232 E, 254 R, 23/254 E, 255 E; 73/27 R; 252/408

[56] References Cited
UNITED STATES PATENTS

| | | |
|---|---|---|
| 3,625,756 | 12/1971 | Taguchi............................. 23/254 E |
| 3,644,795 | 2/1972 | Taguchi............................. 23/254 E |
| 3,695,848 | 10/1972 | Taguchi............................. 23/254 E |
| 3,865,550 | 2/1975 | Bott et al. ......................... 23/254 E |

*Primary Examiner*—R. E. Serwin
*Attorney, Agent, or Firm*—Stewart and Kolasch, Ltd.

[57] ABSTRACT

Gas detecting sensor made of $SnO_2$ characterized by containing less than 5% by weight of at least one of $Al_2O_3$, ZnO, SrO and BaO and less than 1% by weight of chlorine. The gas detecting sensor has a high sensitivity selectively to carbon monoxide but has a low sensitivity to hydrocarbon gases.

6 Claims, 5 Drawing Figures

GAS DETECTING SENSOR

The present invention relates to a gas detecting sensor made of a metallic oxide semiconductor and more particularly to a gas detecting sensor made of a metallic oxide semiconductor having a high sensitivity selectively to carbon monoxide but having a low sensitivity to hydrocarbon gases.

It is already well known that metallic oxide semiconductors such as $SnO_2$, $ZnO$ or $Fe_2O_3$ have a property that, when it adsorbs a such as hydrogen, carbon monoxide or hydrocarbons, its electrical conductivity is increased. By utilizing this property, such metallic oxide semiconductors are used as a gas detecting sensor, for example, in a gas detecting device for preventing explosion or for detecting leakage of gas such as propane gas or town gas which is dangerous to human life.

However, such a gas detecting sensor is so low in sensitivity to carbon monoxide that it is quite useless for detecting carbon monoxide produced by the incomplete combustion of a fuel or for the early discovery of leaking town gas.

As a result of making various investigations on a gas detecting sensor made of $SnO_2$ to increase its sensitivity to carbon monoxide, it has been discovered that its sensitivity to carbon monoxide can be increased by adding chlorine to $SnO_2$. However, its sensitivity to other combustible gases is also increased.

Thus the gas detecting sensor in which $SnO_2$ is made to contain chlorine is sensitive to cabon monoxide but the sensitivity to other combustible gases is also increased. Therefore, it is very difficult to positively detect the low concentration of carbon monoxide.

For example, when 2% by volume of propane gas is present in air, there is a danger of causing an explosion. Therefore, if propane gas in an amount smaller than 0.2% by volume can be positively detected, the gas detecting sensor can be well used. It will be enough if it can detect when about 1,000 p.p.m. of propane gas are usually present in air.

However, even a minor amount of carbon monoxide is detrimental to human health. For example, it is said that, when 50 p.p.m. of carbon monoxide are present in air, it will be impossible to work for more than 8 hours, that, when 200 p.p.m. of carbon monoxide are present in air, a headache will occur in 2 or 3 hours and that, when 2,000 p.p.m. of carbon monoxide are present in air, a human will die in 2 hours. Therefore, a gas detecting sensor that can detect when 100 to 200 p.p.m. of carbon monoxide are present in air is required.

The above-mentioned gas detecting sensor made of $SnO_2$ containing chlorine can wall detect when 100 to 200 p.p.m. of carbon monoxide are present in air but can also detect when 50 to 100 p.p.m. of a hydrocarbon gas are present in air. Therefore, as a result, even if such hydrocarbon gas as, for example, propane, methane or isobutane gas is in a low concentration, it will be detected.

Therefore, the above-mentioned gas detecting sensor is sensitive to a gas present in a home and can detect such gas but can not selectively and positively detect carbon monoxide of a low concentration.

The object of the present invention is to provide a gas detecting sensor made of $SnO_2$ having a high sensitivity selectively to carbon monoxide but having a low sensitivity to hydrocarbon gases.

The present invention comprises a gas detecting sensor made of $SnO_2$ characterized by containing less than 5by weight material selected from the group consisting of at least one of $Al_2O_3$, $ZnO$, $SrO$ and $BaO$ and less than % by weight of chlorine.

In the gas detecting sensor of the present invention, the reason for providing that $SnO_2$ contain less than 5% by weight of at least one of $Al_2O_3$, $ZnO$, $SrO$ and $BaO$ is based on the fact that the sensitivity of $SnO_2$ to such hydrocarbon gases as propane, methane and isobutane is remarkably inhibited when it contains said metallic oxides in the amount specified. However, when it contains more than 5% by weight of said metallic oxides, its sensitivity to carbon monoxide will become inhibited.

In the gas detecting sensor of the present invention, the reason for making $SnO_2$ contain less than 1% by weight of chlorine is based on the fact that, when $SnO_2$ contains chlorine, its sensitivity to various gases such as carbon monoxide gas and hydrocarbon gases such as propane, methane and isobutane is higher than its sensitivity in the case where $SnO_2$ contains no chlorine. However when more than 1% by weight of chlorine is present, the sensitivity will begin to reduce and the stability of the gas detecting sensor will be adversely affected.

Thus, by providing that $SnO_2$ contain less than 5% by weight of at least one of $Al_2O_3$, $ZnO$, $SrO$ and $BaO$ and less than 1% by weight of chlorine, the gas detecting sensor according to the present invention has a high sensitivity selectively to carbon monoxide and has a low sensitivity to hydrocarbon gases.

The raw material used in the gas detecting sensor of the present invention which is produced as is detailed in the examples, is coated on a detecting sensor base and is sintered. Then the characteristics of the gas detecting sensor is measured. The raw material which is mixed with water in a weight ratio of about ½ and with 0.1 to 0.2% by weight of a caking agent such as polyvinyl alcohol or starch so as to have a desirable cosity is coated on a detecting sensor base provided with a heat-proof base plate having two electrodes at both ends, for example, a ceramic carrier. In the example of the present invention, there is used a 3 mm square alumina base plate provided with two spiral iridium wire electrodes at both ends. The thickness of the coating of the raw material may be such as to be continuously connected between both electrodes and is usually about 0.1 to 2 mm. The electrodes at both ends of the ceramic carrier are also heaters and each of them has two terminals so that the raw material on the detecting sensor base may be heated and sintered by passing an electric current between the two terminals of one electrode. The heating temperature can not be accurately measured but is generally 400° to 800°C with a heating electric power of 3 to 5 watts and the optimum value is different depending on the raw material. The sintering may be carried out by maintaining this temperature for 30 minutes to several hours. In such case, it is sintered in air or in $O_2$, $N_2$, $H_2$ or any other combustible gases depending on the raw material.

In the case of using the thus produced sensor, the sensor is heated by connecting a load in series to the sensor electrodes, impressing a voltage and passing an electric current also to the electrodes, and is used while maintained usually at 150° to 400°C. The sensor heating temperature varies depending on the composition of the raw material and the kind of the gas to be detected, but, in the example of the present invention, an optimum sensitivity is obtained at about 200°C.

When a gas comes into contact with the thus produced gas detecting sensor, the resistance value of the sensor will vary, the current will vary and the load will operate. By connecting a resistance with the load and measuring the electric powers at both ends, the resistance value of the sensor can be calculated and the characteristics of the sensor can be determined. In the example of the present invention, the sensor resistance value when no gas is present is expressed in R air, the resistance value of the sensor in a gas is expressed in R gas and the characteristic of the sensor is represented by the ratio of R air/R gas.

The raw material may be sintered on the gas detecting sensor base keeping the base at 400° to 800°C. by passing an electrical current larger than usual to the electrodes or by drying the base coated with the raw material and then keeping it at a required temperature in an electric furnace.

The present invention shall be concretely explained in the following by enumerating an example and comprative example and referring to the accompanying drawings in which.

EXAMPLE 1

1,000cc. of an aqueous solution of 28% $NH_4OH$ were added to an aqueous solution prepared by dissolving 500g. of $SnCl_4$ and 6.1g. of $Al(NO_3)_3$ in 250cc. of water to adjust the PH to 6. The obtained precipitate was separated and dried and was calcined at 600°C for 1 hour in an electric furnace. This calcined product was crushed to a particle size of 100 to 150 mesh (Tyler). This raw material was supplied to coat a gas detecting sensor base and was dried. Then the raw material on the base was sintered by passing an electric current to two electrodes which were provided in the base. Thus a gas detecting sensor containing 0.5% by weight of $Al_2O_5$ and 0.1% by weight of chlorine was obtained.

Figure 1:
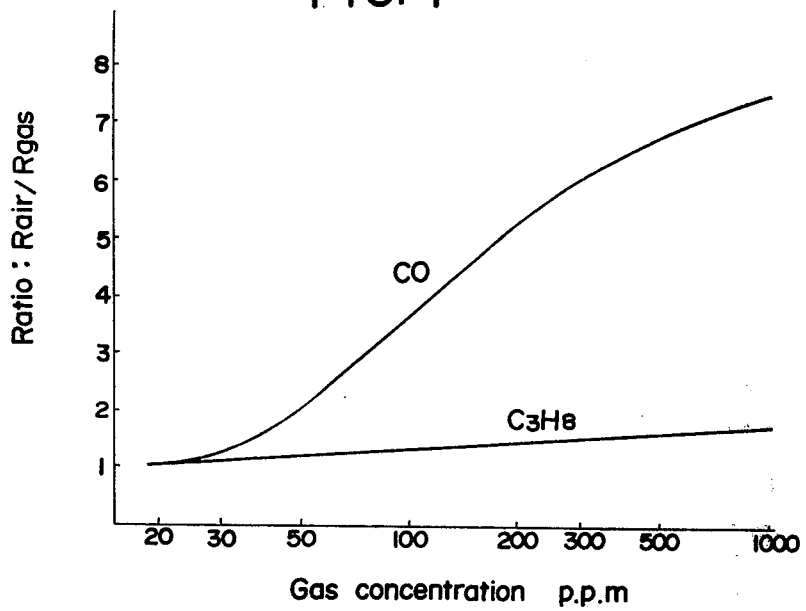
FIG. 1 is a logarithmic curve diagram showing the variations of the resistance values of an embodiment of the gas detecting sensor of the present invention at respective concentrations of carbon monoxide and propane.

The variations of the electrical resistance values of the obtained gas detecting sensor at respective concentrations of carbon monoxide (CO) and propane ($C_3H_8$) are as shown in FIG. 1.

EXAMPLE 2

50cc. of an aqueous solution of 35% hydrochloric acid were added to a mixture of 500g. of $SnCl_4$ and 6g. of ZnO and then were neutralized by adding 1,000cc. of an aqueous solution of 28% $NH_4OH$. The obtained precipitate was separated and dried. The dried precipitate was calcined in an electric furnace at the temperature of 500°C for one hour and then the calcined product was crushed to a particle size of 100 to 150 mesh (Tyler). This raw material was applied to coat a gas detecting sensor base and was dried. Then the raw material on the base was sintered by passing an electric current to two electrodes which were provided in the base. Thus a gas detecting sensor containing 0.2% by weight of ZnO and 0.2% by weight of chlorine was obtained.

Figure 2:
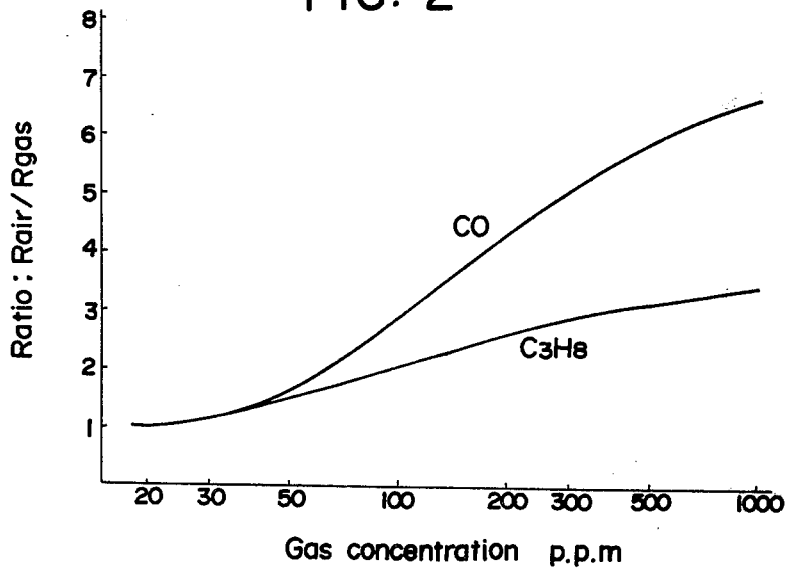
FIG. 2 is a logarithmic curve diagram showing the variations of the resistance values of another embodiment of the gas detecting sensor of the present invention at respective concentrations of carbon monoxide and propane.

The variations of the electrical resistance values of the obtained gas detecting sensor at respective concentrations of carbon monoxide (CO) and propane ($C_3H_8$) are as shown in FIG. 2.

EXAMPLE 3

500g. of $SnO_2$ were mixed with 50cc. of an aqueous hydrochloric acid and 15g. of $SrCO_3$ and the whole was heated at the temperature of 70°C and the obtained reaction product was dried to solidify. The solified product was calcined in an electric furnace at the temperature of 500°C for one hour. The calcined product was crushed to a particle size of 100 to 150 mesh (Tyler). This raw material was applied to coat a gas detecting sensor base and was dried. Then the raw material on the base was sintered by passing an electric current to two electrodes which were provided in the base. Thus a gas detecting sensor containing 3% by weight of SrO and 0.8% by weight of chlorine.

Figure 3:
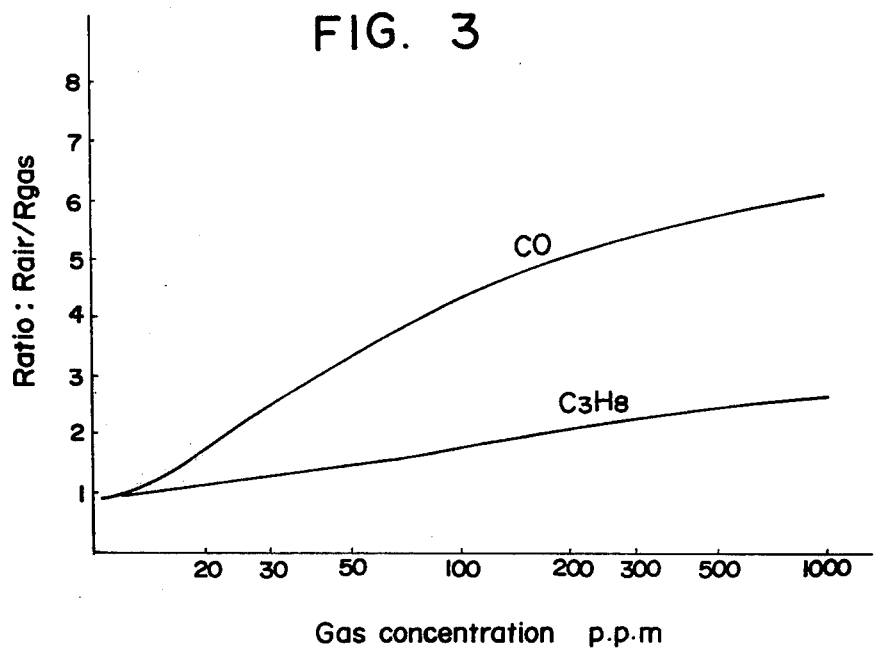
FIG. 3 is a logarithmic curve diagram showing the variations of the resistance values of a further embodiment of the gas detecting sensor of the present invention at respective concentrations of carbon monoxide and propane.
Figure 4:
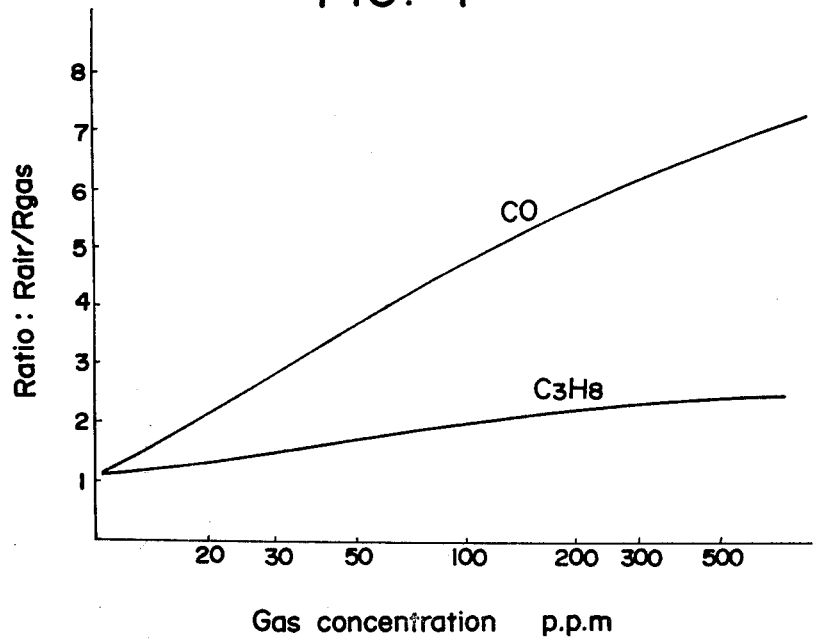
FIG. 4 is a logarithmic curve diagram showing the variations of the resistance values of a still further embodiment of the gas detecting sensor of the present invention at respective concentrations of carbon monoxide and propane.

The variations of the electric resistance values of the obtained gas detecting sensor at respective concentrations of carbon monoxide (CO) and propane ($C_3H_8$) are as shown in FIG. 3.

EXAMPLE 4

50cc. of an aqueous solution of 35% hydrochloric acid were added to a mixture of 500g. of $SnCl_4$ and 8g. of $BaCO_3$ to completely dissolve the latter into the farmer. Then the obtained solution was added with 1,000cc. of an aqueous solution of 28% $NH_4OH$ to obtain a precipitate. The precipitate was applied to coat a gas detecting sensor base and was dried. Then the precipitate on the base was sintered by passing an electric current to two electrodes which were provided in the base. Thus a gas detecting sensor containing 2% by weight of BaO and 0.4% by weight of chlorine.

The variations of the electric resistance values of the obtained gas detecting sensor at respective concentrations of carbon monoxide (CO) and propane ($C_3H_8$) are as shown in FIG. 2.

COMPARATIVE EXAMPLE

Figure 5:
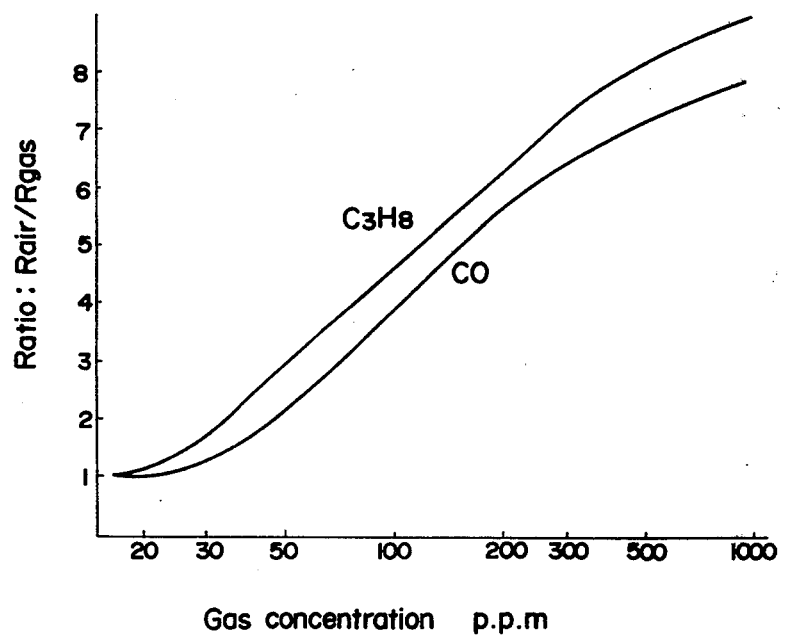
FIG. 5 is a logarithmic curve diagram showing the variations of the resistance values of a gas detecting sensor of the control at respective concentrations of carbon monoxide and propane.

The variations of the resistance values of an $SnO_2$ gas detecting sensor containing 0.1% by weight chlorine at respective concentrations of carbon monoxide (CO) and propane ($C_3H_8$) are as shown in FIG. 5.

As evident from the curve diagrams shown in FIGS. 1, 2, 3 and 4 respectively on Examples 1, 2, 3 and 4 it is recognized that the gas detecting sensor according to the present invention can detect carbon monoxide very sensitively but shows substantially no senstivity to propane.

On the other hand, as shown in FIG. 5, it is recognized that the gas detecting sensor of the comparative example has a practical sensitivity to carbon monoxide but has a sensitivity to propane higher than to carbon monoxide and has no high sensitivity slectively to carbon monoxide.

What we claim is:

1. A gas detecting means comprising $SnO_2$ containing from more than 0% by weight to less than 5% by weight of at least one material selected from the group consisting of $Al_2O_3$, ZnO, SrO and BaO and from more than 0% by weight to less than 1% by weight of chlorine.

2. The gas detecting sensor of claim 1 containing 0.5% by weight of $Al_2O_3$ and 0.1% by weight of chlorine.

3. The gas detecting sensor of claim 1 containing 0.2% by weight of ZnO and 0.2% by weight of chlorine.

4. The gas detecting sensor of claim 1 containing 3% by weight of SrO and 0.8% by weight of chlorine.

5. The gas detecting sensor of claim 1 containing 2% by weight of BaO and 0.4% by weight of chlorine.

6. A gas detecting sensor comprising $SnO_2$ containing about 0.2 to 5% by weight of at least one material selected from the group consisting of $Al_2O_3$, ZnO, SrO and BaO and about 0.1 to less than 1% by weight of chlorine.

* * * * *